US00PP30636P3

(12) United States Plant Patent
Berry

(10) Patent No.: US PP30,636 P3
(45) Date of Patent: Jul. 2, 2019

(54) ***HIBISCUS* PLANT NAMED 'JBG 14015'**

(50) Latin Name: *Hibiscus rosa-sinensis*
Varietal Denomination: JBG 14015

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,304

(22) Filed: Aug. 2, 2018

(65) Prior Publication Data

US 2019/0045689 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
See application file for complete search history.

*Primary Examiner* — Annette H Para
(74) *Attorney, Agent, or Firm* — The Webb Law Firm

(57) ABSTRACT

A new and distinct *Hibiscus* plant having red colored flowers with white/yellow colored highlights that last for several days on the plant over a long flowering season.

1 Drawing Sheet

Botanical classification: *Hibiscus rosa-sinensis.*
Varietal denomination: 'JBG 14015'.

BACKGROUND OF THE INVENTION

The present invention comprises a new and distinct *Hibiscus* plant having the varietal name 'JBG 14015'. The new variety is the result of a planned breeding program with the purposes of developing *Hibiscus rosa-sinensis* plants that exhibit pathogen resistance, multi-day flowers with unique coloration, and possess desirable production traits. 'JBG 14015' is the result of a cross conducted in Grand Saline, Tex. between *Hibiscus rosa-sinensis* varieties 'JBGRH-KNT' (female parent, unpatented) and 'JBG 784' (male parent, unpatented). The new variety was selected in December of 2013 in Grand Saline, Tex. and the first asexual reproduction of the new variety was conducted by semi-mature, softwood cuttings in October of 2014 in Grand Saline, Tex. 'JBG 14015' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14015' is similar to its female parent in having red colored flowers with overlapping petals, but differs from its female parent in having white/yellow colored highlights across the flower and an increased vigor. 'JBG 14015' is similar to its male parent in having red colored flowers with overlapping petals, but differs from its male parent in having a lighter colored flower center and petals that do not curl forward when the flowers open.

When 'JBG 14015' is compared to *Hibiscus rosa-sinensis* variety 'JBG 14006' (U.S. Plant patent application Ser. No. 15/998,307), both varieties exhibit red colored flowers with overlapping petals. However, the flowers of 'JBG 14015' are a darker red color than 'JBG 14006'. Further, the petals of 'JBG 14006' are more overlapping and ruffled in appearance than 'JBG 14015'.

The following traits distinguish 'JBG 14015' as a new and distinct cultivar from other *Hibiscus* varieties known to the breeder:

1. Red colored flowers with white/yellow colored highlights;
2. Overlapping flower petals;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3$^{rd}$ Edition, except where general color terms are used.

PLANT

Time to initiate roots: About 45 days at an average of 24° C.
Time to develop roots: About 52 days at an average of 24° C.

Time to produce a finished flowering plant from a rooted cutting: About 30 weeks in a 24.0 cm diameter container.
Specific disease/pest resistance: Resistance to bacterial leaf spot (*Pseudomonas* spp.).
Heat/cold tolerance: Nothing unusual noted to date.
Drought tolerance: Nothing unusual noted to date.
Plant:
*Type.*—Tropical, ornamental shrub.
*Habit.*—Upright.
*Height.*—150.0 cm at maturity.
*Spread.*—90.0 cm at maturity.
*Vigor.*—Strong.
Rooting vigor: Very strong.
Stem:
*Number per plant.*—9.
*Length.*—Ranging from 46.0-65.5 cm.
*Width.*—5.0-9.0 mm.
*Texture.*—Immature: Smooth. Mature: Vertically ridged.
*Strength.*—High.
*Branch number.*—Moderate with a vase-shape; 9.
*Internode length.*—2.5-3.0 cm.
*Color.*—Immature: 144B. Mature: 199B.
*Stipules.*—Number per node: 2. Shape: Linear. Length: 1.0 cm. Width: 1.0 mm. Surface texture: Smooth. Apex: Acute. Base: Linear. Margin: Entire. Color: 138B.
Foliage:
*Arrangement.*—Alternate; simple.
*Size of leaf.*—Length: 10.7 cm. Width: 9.3 cm.
*Shape of leaf* (*generally*).—Ovate.
*Shape of apex.*—Acute.
*Shape of base.*—Rounded.
*Texture* (*both surfaces*).—Smooth.
*Margin type.*—Crenate.
*Color.*—Young leaves: Upper surface: 138A. Lower surface: 143A. Mature leaves: Upper surface: 138A. Lower surface: 143A.
*Veins.*—Venation type: Pinnate. Color: Upper surface: 143A. Lower surface: 143C.
*Petiole.*—Length: 3.0 cm. Diameter: 3.0 mm. Texture: Smooth. Color: 138A.

FLOWERS

Buds (described one day before flowering):
*Shape.*—Lanceolate.
*Diameter.*—2.5 cm.
*Length.*—6.5 cm.
*Color.*—181B.
Natural flowering season: From spring through fall in Grand Saline, Tex.
Flower type and habit: Single, with overlapping petals.
Fragrance: None observed.
Flowers (described on the first day of opening):
*Number per stem.*—1.
*Overall depth.*—10.5 cm.
*Overall diameter.*—14.5 cm.
*Shape.*—Rotate; regular.
*Lastingness.*—3 days on the plant.
*Petals.*—Number: 5. Arrangement: Simple. Length: 9.0 cm. Width: Apex: 7.9 cm. Base: 3.7 cm. Shape: Ovate. Apex: Obtuse. Base: Cuneate. Margin: Entire. Texture/appearance: Upper surface: Smooth. Lower surface: Smooth. Color: When opening and fully opened: Upper surface: 43A with 15C highlights at the apex through the center and 46A at the throat. Lower surface: 42A at the apex through the center and 13C at the base.
*Calyx.*—Form: Fused. Overall length: 3.2 cm. Overall diameter: 2.5 cm. Sepals/calyx lobes: Number: 5. Shape: Lanceolate. Apex: Acute. Margin: Entire. Texture: Slightly pubescent. Color: Outer surface: 137C. Inner surface: 138B.
*Epicalyx.*—Length: 1.5 cm. Width: 4.0 mm. Texture: Smooth. Color: 137B.
*Bracts.*—Not present.
*Peduncle.*—Length: 6.4 cm. Diameter: 4.0 mm. Strength: Strong. Angle: 45°. Texture: Smooth. Color: 144A.
Reproductive organs:
*Gynoecium.*—Pistils: Number: 1. Length: 10.0 cm. Stigma: Number: 5. Shape: Round. Length: 6.0 mm. Diameter: 3.0 mm. Color: 30C. Style: Length: 7.5 cm. Width: Apex: 4.0 mm. Base: 9.0 mm. Color: 16B at the apex to 33B at the base. Ovary: Shape: Ovate. Length: 1.5 cm. Width: Apex: 3.0 mm. Base: 7.0 mm. Color: 4C.
*Androecium.*—Stamens: Number: 78. Position: Just below the stigma on the style. Anther: Shape: U-shaped. Diameter: 2.0 mm. Color: 23A. Filament: Length: 6.0 mm. Width: 1.0 mm. Color: 23C. Pollen: Color: 23A. Amount (generally): Heavy.

SEEDS

Seeds:
*Number.*—From 0 to 20.
*Color.*—200C.
*Length.*—5.0 mm.
*Width.*—5.0 mm.

I claim:
1. A new and distinct variety of *Hibiscus* plant, as is herein illustrated and described.

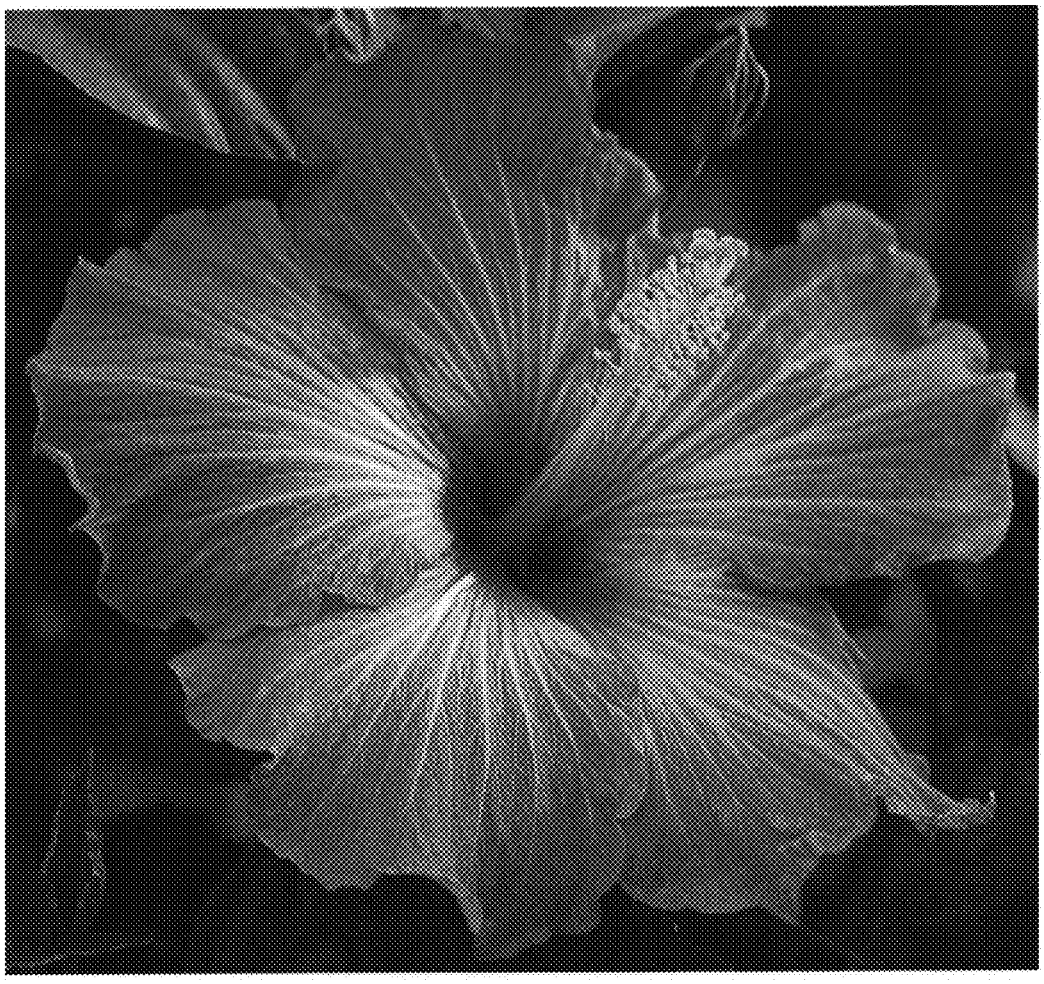

* * * * *